US006319392B1

(12) United States Patent
Navarro

(10) Patent No.: US 6,319,392 B1
(45) Date of Patent: Nov. 20, 2001

(54) COAL TAR EXTRACT WITH REDUCED AROMATIC HYDROCARBON CONTENT, METHOD FOR OBTAINING SAME AND DERMATOLOGICAL AND COSMETIC COMPOSITIONS

(75) Inventor: Roger Navarro, Pamiers (FR)

(73) Assignee: Pierre Fabre Dermo-Cosmetique, Boulogne-Billancourt (FR)

( * ) Notice: Subject to any disclaimer, the term of this patent is extended or adjusted under 35 U.S.C. 154(b) by 0 days.

(21) Appl. No.: 09/380,958

(22) PCT Filed: Mar. 11, 1998

(86) PCT No.: PCT/FR98/00488

§ 371 Date: Sep. 10, 1999

§ 102(e) Date: Sep. 10, 1999

(87) PCT Pub. No.: WO98/40447

PCT Pub. Date: Sep. 17, 1998

(30) Foreign Application Priority Data

Mar. 11, 1997 (FR) .................................................. 97 02825

(51) Int. Cl.⁷ ............................... C10C 1/20; C10C 3/02; C10C 1/04; C10C 3/06; A61K 35/78
(52) U.S. Cl. ........................... 208/44; 208/41; 424/196.1; 424/401; 424/405; 514/861; 514/863; 514/864; 514/880; 514/881
(58) Field of Search ..................................... 424/401, 405, 424/196.1; 514/861, 863, 864, 880, 881; 208/41, 44

(56) References Cited

U.S. PATENT DOCUMENTS

| 3,928,579 | * | 12/1975 | McShane | 424/167 |
| 4,409,094 | | 10/1983 | Longwell . | |
| 4,608,127 | * | 8/1986 | Sakuma et al. | 203/48 |
| 5,262,043 | | 11/1993 | Boenigk . | |
| 5,746,906 | * | 5/1998 | McHenry et al. | 208/22 |
| 6,010,617 | * | 1/2000 | Mackerer et al. | 208/44 |

FOREIGN PATENT DOCUMENTS

| 4119170 | * | 12/1992 | (DE) . |
| 0465434A | | 1/1992 | (EP) . |

OTHER PUBLICATIONS

Zielinski, J. et al., "Benzo(.alpha.)pyrene in Petroleum and Coal–Tar Products", Chem. Abs. vol. 123:117694 (1995).
Database WPI, XP002047458 & JP 55 153 710 A (Fujinaga Seiyaku KK), Nov. 29, 1980.

\* cited by examiner

Primary Examiner—Jose'G. Dees
Assistant Examiner—Marina Lamm
(74) Attorney, Agent, or Firm—The Firm of Hueschen and Sage; G. Patrick Sage

(57) ABSTRACT

The invention concerns a coal tar extract with reduced polycyclic aromatic hydrocarbon and benzo(a)pyrene content and a method for obtaining same using two sequentially linked distillation systems. The invention also concerns cosmetic and dermatological preparations containing said resulting coal tar extract.

1 Claim, No Drawings

COAL TAR EXTRACT WITH REDUCED AROMATIC HYDROCARBON CONTENT, METHOD FOR OBTAINING SAME AND DERMATOLOGICAL AND COSMETIC COMPOSITIONS

The present application is a U.S. National Application filed under 35 USC 371 of PCT/FR98/00488, filed Mar. 11, 1998 based upon French application Serial No. 97/02835 filed Mar. 11, 1997.

The present invention relates to a coal tar extract with a reduced content of polycyclic aromatic hydrocarbons, to a process for obtaining it and to dermocosmetic compositions containing it.

The term "coal tar" means the by-product of the destructive distillation of bituminous coal distilling between at 300 and 370° C. This is a black viscous liquid whose characteristic odor resembles that of naphthalene.

The term "coal pitch" means the residue from the distillation of coal tar.

Crude coal tar contains a large proportion of polycyclic aromatic hydrocarbons (PAH) of the order of 100,000 ppm. Among the predominant PAHs which have been identified are fluoranthene, pyrene, anthracene, phenanthrene, fluorene, 1,2-benzofluorene, 2,3-benzofluorene, 1,2-benzanthracene, chrysene, benzo(k)fluoranthene, benzo(a) fluoranthene, benzo(b)fluoranthene, benzo(e)pyrene, benzo (a)pyrene (BaP), indeno(1,2,3,c,d)pyrene, 1,2,5,6-dibenzanthracene, benzo(6)chrysene and benzo(g,h,i) perylene, the last thirteen compounds having toxic properties.

Coal tar is commonly used in antidandruff treatment, in the treatment of certain types of dermatitis such as eczema, lichenification and psoriasis. Before being incorporated into dermatological compositions, coal tar undergoes a purification intended to make it colorless, odorless and substantially free of irritant properties.

Many processes for purifying coal tar are described in the literature.

U.S. Pat. No. 3,766,052 (Warner Lambert Co.) published on Oct. 16, 1973 describes a process for purifying commercially available coal tar, which comprises mixing the said coal tar with a $C_{15}$–$C_{22}$ fatty acid ester, adding squalane or squalene, and recovering the purified coal tar in the form of the supernatant liquid. The coal tar obtained has a viscosity of between 10 and 50 mpa.s and a density at 25° C. of between 0.88 and 0.95. It is used as an active ingredient in dermatological compositions in a proportion from 1 to 10% by weight.

U.S. Pat. No. 3,928,579 (Warner Lambert Co.) published on Dec. 23, 1975 describes a process for purifying crude coal tar, which consists:

1) of an extraction with a volatile solvent or mixture of solvents whose kauri butanol number is less than 75 and whose boiling point is less than 80° C.,
2) of a filtration, and then
3) of an evaporation of the volatile solvent(s). The solvents used are $C_3$–$C_6$ alkanes or CFCs. The purified coal tar is incorporated in the dermatological composition.

Patent application JP-55 153 710 (Fujunaga Seiyaku) published on Nov. 30, 1980 describes a cosmetic skin composition containing, as active ingredient, purified tar obtained by distillation of mineral, animal or plant tar under reduced pressure, by diazotization and then by hydrolysis or heating. The tars used are coal tar and soybean tar.

The distillation carried out from 50 to 120° C. under a vacuum of 5–10 mmHg allows the mutagenic properties of the tar to be reduced by a factor of 20. Diazotization with an excess of nitrite followed by an increase in temperature and optionally a hydrolysis makes it possible to reduce the mutagenic properties of the tar by a factor of 90.

Among the PAHs contained in coal tar whose toxic properties have been recognized, it has been found that BaP exhibits carcinogenic properties in the event of prolonged use.

Patent application EP-A-465,434 describes tar oil obtained by fractional distillation of naphthalene oil on three rectification columns in series between 230 and 330° C. . The naphthalene oil itself is obtained from the distillation of coal pitch.

At the experimental stage, this extract can contain a BaP percentage of less than 2 ppm (parts per million). However, at the industrial scale, a BaP percentage of about 20 ppm will be selected.

The present invention relates to a coal tar extract with a reduced content of both PAH and BaP.

The coal tar extract according to the invention is characterized by a maximum PAH content of about ten ppm and by a maximum BaP content of about a few ppm.

The coal tar extracted according to the invention is preferably characterized by a PAH content of less than about 4 ppm and a BaP content of less than about 1 ppm.

The present invention also relates to a process for obtaining the said coal tar extract from crude coal tar which uses at least two distillation systems connected in series.

A thin-film evaporator is advantageously chosen as the first distillation system, and/or a distillation column as the second system.

The distillation on a thin-film evaporator is carried out under a pressure of 5 to 7 mmHg, at a temperature of between 198 and 200° C. , and at a crude coal tar feed rate equal to 18 to 19 kg/h.

The column distillation following distillation on a thin-film evaporator is carried out at between 260 and 320° C.

The distillation yield according to the invention using a thin-film evaporator coupled to a distillation column is between 20 and 25% by weight.

Crude coal tar is commercially available and corresponds to the definition in the French Pharmacopea and/or in the US Pharmacopea. Its respective contents of PAH and of BaP are about 93,000 and 2000–10,000 ppm.

The present invention relates to cosmetic or dermatological compositions containing the coal tar extract according to the invention, preferably in a proportion of from 0.1 to 10% by weight.

A cosmetic or dermatological composition containing 0.5% of coal tar extract with 1 ppm of BaP has respective contents of PAH and BaP of about 15 and 2 ppb (parts per billion).

The said compositions are proposed under the same therapeutic indications as crude coal tar.

The examples which follow illustrate the invention without limiting its scope.

EXAMPLE 1:SHAMPOO

| | |
|---|---:|
| PURIFIED WATER qs | 100 g |
| PULVERIZED SALICYLIC ACID | 1.50 g |
| UNDECYLENIC DERIVATIVE | 1 to 3 g |
| QUATERNARY POLYMER | 0.5 to 1 g |
| ETHOXYLATED SODIUM ALKYL SULFATE | 9 g |
| POLYSORBATE-20 | 5 to 7 g |
| FATTY ACID ETHANOLAMIDE | 5 g |
| PEG-6000 DISTEARATE | |
| ALKYLAMIDO BETAINE | 1.5 g |
| COCOAMPHODIACETATE | 3.5 g |
| DISODIUM EDTA | 0.2 g |

-continued

| | |
|---|---|
| 20 POE SORBITAN MONOLAURATE | 5 g |
| FRAGRANCE | QS |
| DYE | QS |
| COAL TAR | 0.1 → 2.50 g |

EXAMPLE 2:SHAMPOO

| | |
|---|---|
| WATER qs | 100 g |
| SODIUM LAURETH SULFATE | 8 g |
| POLYSORBATE | 7 g |
| PEG-150 DISTEARATE | 4 g |
| SODIUM UNDECYLENAMIDO MEA-SULFOSUCCINATE | 3 g |
| SODIUM COCOAMPHODIACETATE | 3 g |
| SALICYLIC ACID | 1.5 g |
| FRAGRANCE | 0.5 g |
| T.E.A.-HYDROLYZED COCOYL-COLLAGEN | 1 g |
| COAL TAR | 0.1 → 1 g |

EXAMPLE 3:LOTION

| | |
|---|---|
| WATER qs | 100 ml |
| SD-ALCOHOL 39-C | 63 ml |
| FRAGRANCE | 0.20 g |
| VINYL ACETATE/CROTONIC ACID COPOLYMER | 0.15 g |
| PEG-13 OCTANOATE | 0.10 g |
| LAURYLPYRIDINIUM CHLORIDE | 0.05 g |
| COAL TAR | 0.1 → 1 g |

EXAMPLE 4:CREAM

| | |
|---|---|
| WATER qs | 100 g |
| PEG-40 SORBITAN LANOLATE | 7.5 g |
| PARAFFIN | 5 g |
| PROPYLENE GLYCOL | 5 g |
| CETYL ALCOHOL | 3 g |
| POLYSORBATE | 3 g |
| LANOLIN | 2 g |
| SALICYLIC ACID | 1.5 g |
| FRAGRANCE | 0.4 g |
| COAL TAR | 0.1 → 3 g |

EXAMPLE 5:OIL

| | |
|---|---|
| MINERAL OIL qs | 100 g |
| DIBUTYL ADIPATE | 15 g |
| CAPRYLIC/CAPRIC TRIGLYCERIDE | 10 g |
| COAL TAR | 0.1 → 2 g |

EXAMPLE 6:SYNDET

| | | |
|---|---|---|
| SODIUM HEMISULFOSUCCINATE | qs | 100 g |
| SODIUM ISOTHIONATE | | 20 g |
| WAX OF MINERAL ORIGIN | | 12 g |
| CETYL ALCOHOL | | 13 g |

-continued

| | |
|---|---|
| WHEAT STARCH | 20 g |
| PINE TAR | 0.3 g |
| CADE TAR | 0.3 g |
| SALICYLIC ACID | 2 g |
| ZINC OXIDE | 5 g |
| COAL TAR | 0.1 → 2 g |

EXAMPLE 7:MOUSSE

| | |
|---|---|
| DEMINERALIZED WATER qs | 100 g |
| GUAR GUM | 0.10 g |
| JOJOBA OIL | 2 g |
| ETHYLHEXYL P-METHOXYCINNAMATE | 1 g |
| VINYLPYRROLIDONE/DMAE METHACRYLATE | 1 g |
| PVP HEXADECENE COPOLYMER | 2 g |
| DIMETHYL/TRIMETHYL-POLYSILOXANE | 1 g |
| CETRIMONIUM BROMIDE | 0.40 g |
| FRAGRANCE | 0.15 g |
| COAL TAR | 0.1 → 2 g |

EXAMPLE 8:EMOLLIENT SOLUTION

| | |
|---|---|
| PROPYLENE GLYCOL qs | 100 g |
| CADE TAR | 10 g |
| PINE TAR | 10 g |
| POLYSORBATE | 20 g |
| POLYETHOXYLATED COCONUT FATTY ESTERS | 10 g |
| POLYETHOXYLATED ALKYLPHENOL | 10 g |
| FRAGRANCE | 1 g |
| COAL TAR | 0.1 → 5 g |

EXAMPLE 9:GELLED BODY OIL

| | |
|---|---|
| CAPRYLIC/CAPRIC TRIGLYCERIDE | 20 g → 30 g |
| MINERAL OIL | 36 g |
| PETROLATUM | 15 g |
| PEG-40 SORBITOL HEXAOLEATE | 8 g |
| QUATERNIUM-18 HECTORITE | 5 g |
| HYDROGENATED TALLOWETH-60 MYRISTYL GLYCOL | 5 g |
| FRAGRANCE | 0.5 g |
| BENZOIC ACID | 0.3 g |
| PROPYL GALLATE | 0.02 g |
| COAL TAR | 0.1 → 2 g |

What is claimed is:
1. A process for obtaining a coal tar extract from crude coal tar, which employs a thin-film evaporator and a distillation column, wherein a first distillation of the crude coal tar is carried out on a thin-film evaporator under a pressure of 5 to 7 mm Hg, at a temperature between 198 and 200° C., and at a crude coal tar feed rate of 18 to 19 kg/h, and wherein this first distillation is then followed by a second distillation of the product of the first distillation on a distillation column at a temperature of 260 to 320° C., and wherein a polycyclic aromatic hydrocarbon content of the coal tar extract thus produced is less than 4 ppm and a benzo(a)pyrene content of the coal tar extract thus produced is less than 1 ppm.

* * * * *

UNITED STATES PATENT AND TRADEMARK OFFICE
CERTIFICATE OF CORRECTION

PATENT NO.   : 6,319,392 B1
DATED        : November 20, 2001
INVENTOR(S)  : Roger Navarro It is certified that error appears in the above-identified patent and that said Letters Patent is hereby corrected as shown below:

<u>Title page,</u>
Item [30], Foreign Application Priority Data, "9702825" should be -- 9702835 --.

Signed and Sealed this

Twentieth Day of January, 2004

JON W. DUDAS
*Acting Director of the United States Patent and Trademark Office*